(12) United States Patent
Feng et al.

(10) Patent No.: US 12,163,144 B2
(45) Date of Patent: Dec. 10, 2024

(54) USE OF SOYBEAN BROAD-SPECTRUM DISEASE RESISTANCE RELATED GENE

(71) Applicant: Northeast Institute of Geography and Agroecology, Chinese Academy of Sciences, Jilin (CN)

(72) Inventors: Xianzhong Feng, Jilin (CN); Suxin Yang, Jilin (CN); Dongmei Wang, Jilin (CN); Hui Yu, Jilin (CN)

(73) Assignee: Northeast Institute of Geography and Agroecology, Chinese Academy of Sciences, Jilin (CN)

( * ) Notice: Subject to any disclaimer, the term of this patent is extended or adjusted under 35 U.S.C. 154(b) by 251 days.

(21) Appl. No.: 17/597,717

(22) PCT Filed: Jul. 30, 2020

(86) PCT No.: PCT/CN2020/105801
§ 371 (c)(1),
(2) Date: Jan. 19, 2022

(87) PCT Pub. No.: WO2021/082567
PCT Pub. Date: May 6, 2021

(65) Prior Publication Data
US 2022/0243218 A1 Aug. 4, 2022

(30) Foreign Application Priority Data
Oct. 30, 2019 (CN) .......................... 201911044883.5

(51) Int. Cl.
*C12N 15/82* (2006.01)
*C07K 14/415* (2006.01)

(52) U.S. Cl.
CPC ........ *C12N 15/8282* (2013.01); *C07K 14/415* (2013.01)

(58) Field of Classification Search
None
See application file for complete search history.

(56) References Cited

FOREIGN PATENT DOCUMENTS

| CN | 103103202 A | 5/2013 |
|---|---|---|
| CN | 104726457 A | 6/2015 |
| CN | 108588087 A | 9/2018 |
| CN | 110317250 A | 10/2019 |
| CN | 110317795 A | 10/2019 |
| CN | 110713528 A | 1/2020 |
| WO | 2015/017786 A1 | 2/2015 |

OTHER PUBLICATIONS

Duan et al., Reactive oxygen species mediate pollen tube rupture to release sperm for fertilization in *Arabidopsis*, (Jan. 2014), Nature Communications, vol. 5, Article No. 3129, pp. 1-10. (Year: 2014).*
Kanduc, D., Homology, similarity, and identity in peptide epitope immunodefinition, 2012, Journal of Peptide Science, vol. 18, pp. 487-494. (Year: 2012).*
Wang, et al., A malectin-like receptor kinase regulates cell death and pattern-triggered immunity in soybean, 2020, EMBO Reports, vol. 21, pp. 1-16. (Year: 2020).*
Zhang et al., Nematode RALF-like 1 targets soybean malectin-like receptor kinase to facilitate parasitism, 2021, Frontiers in Plant Science, vol. 12, pp. 1-13. (Year: 2021).*
Zhang et al., Races of Phytophthora sojae and Their Virulences on Soybean Cultivars in Heilongjiang, China, 2010, Plant Disease, vol. 94(1), pp. 87-91. (Year: 2010).*
Skinner et al., Potential use of additivity of mutational effects in simplifying protein engineering, 1996, Proceedings of the National Academy of Sciences, vol. 93, pp. 10753-10757. (Year: 1996).*
Kim et al., Assembly of mutations for improving thermostability of *Escherichia coli* AppA2 phytase, 2008, Applied Microbiology and Biotechnology, vol. 79, pp. 751-758. (Year: 2008).*
Amin et al., "Characterization and Rapid Gene-Mapping of Leaf Lesion Mimic Phenotype of spl-1 Mutant in Soybean (*Glycine max* (L.) Merr.)", International Journal of Molecular Sciences, vol. 20, No. 2193 (May 3, 2019) 23 pages.
International Search Report from International Application No. PCT/CN2020/105801, mailed Oct. 28, 2020, 10 pages.
International Written Opinion from International Application No. PCT/CN2020/105801, mailed Oct. 28, 2020, 4 pages.
Keinath et al., "PAMP (Pathogen-associated Molecular Pattern)-induced Changes in Plasma Membrane Compartmentalization Reveal Novel Components of Plant Immunity", The Journal of Biological Chemistry, vol. 285, No. 50, (Dec. 10, 2010) pp. 39140-39149.
Kessler et al., "Conserved Molecular Components for Pollen Tube Reception and Fungal Invasion", Science, vol. 330, No. 968 (Nov. 12, 2010) 16 pages.
Liao et al., "FERONIA Receptor Kinase at the Crossroads of Hormone Signaling and Stress Responses", Plant & Cell Physiology, 0(0) (Apr. 19, 2017) pp. 1-8.

(Continued)

*Primary Examiner* — Weihua Fan
*Assistant Examiner* — Christina L Meadows
(74) *Attorney, Agent, or Firm* — TraskBritt

(57) ABSTRACT

The GmLMM1 gene, which is involved in the regulation of PTI immune responses, *Phytophthora* resistance, bacterial blight of soybean disease, soybean halo disease, etc., is cloned in soybeans. The PTI immune response and pathogen resistance of plants can be negatively regulated via the GmLMM1 gene. By reducing the expression of GmLMM1, the PTI immune response of plants can be effectively enhanced, and the pathogen resistance of plants can be increased. Cloning and functional discovery of the GmLMM1 gene provide important foundations and theoretical support for research on the related mechanisms of soybean disease resistance and provide valuable genetic resources for advancing the research and application of plant defense systems. Additionally, cloning and functional delivery of the GmLMM1 gene allows for breeding new soybean varieties with high disease resistance.

3 Claims, 3 Drawing Sheets
Specification includes a Sequence Listing.

(56) References Cited

OTHER PUBLICATIONS

NCBI. "Feronia receptor-like kinase [Glycine max], NCBI Reference Sequence:NP_001237588. 1", NCBI (Oct. 18, 2018) 2 pages.
Schmutz et al., "Hypothetical protein GLYMA_13G054400 [Glycine max], Genbank:KRH18365. 1", NCBI (Jul. 24, 2018) 2 pages.
Chinese First Office Action for Chinese Application No. 201911044883.5, dated Jan. 5, 2021, 10 pages with translation.
Chinese Notification to Grant Patent Right for Invention for Chinese Application No. 201911044883.5, dated Apr. 13, 2021, 3 pages with translation.
Chinese Search Report for Chinese Application No. 201911044883.5, dated Oct. 30, 2019, 7 pages with translation.
Chinese Supplementary Search Report for Chinese Application No. 201911044883.5, dated Oct. 30, 2019, 4 pages with translation.

\* cited by examiner

SEQUENCE LISTING

```
<160> NUMBER OF SEQ ID NOS: 5

<210> SEQ ID NO 1
<211> LENGTH: 896
<212> TYPE: PRT
<213> ORGANISM: Glycine max

<400> SEQUENCE: 1

Met Arg Leu Leu Ser Ile Ile Thr Thr Ser Leu Thr Leu Phe Phe Leu
1               5                   10                  15

Leu Leu Phe Leu Ser Ile Glu Leu Gln Ala Tyr Thr Pro Glu Asp Asn
                20                  25                  30

Phe Thr Ile Ser Cys Gly Thr Thr Gly Ile Val Phe Asp Gly Gln Arg
            35                  40                  45

Thr Trp Thr Gly Asp Ala Asp Thr Lys Tyr Leu Ser Gly Gly Gln Gly
        50                  55                  60

Ser Thr Val Leu Thr Gln Ala Ala Thr Gln Asp Pro Ser Val Asn Gln
65                  70                  75                  80

Val Pro Tyr Thr Thr Ala Arg Leu Ser Pro Ser Gln Phe Asn Tyr Ser
                85                  90                  95

Phe Pro Val Ser Ala Gly Pro Lys Phe Val Arg Leu Phe Phe Tyr Pro
            100                 105                 110

Ala Asp Tyr Pro Ser Phe Pro Arg Thr Asp Ala Ser Phe Ser Val Gln
        115                 120                 125

Ser Asn Gly Phe Thr Phe Leu Lys Gly Phe Asn Ala Ser Leu Asn Ala
    130                 135                 140

Asp Ala Glu Ala Thr Lys Thr Ile Phe Arg Glu Tyr Val Val Asn Val
145                 150                 155                 160
```

```
Asn Asp Gly Glu Thr Leu Ile Leu Ser Phe Thr Pro Ser Gln Pro Asn
            165                 170                 175

Ser Tyr Ala Phe Ile Asn Gly Ile Glu Val Leu Ser Met Pro Ser Asp
        180                 185                 190

Leu Tyr Tyr Thr Ser Ala Thr Asp Ser Thr Gly Phe Lys Phe Leu Gly
            195                 200                 205

Ser Thr Thr Leu Tyr Ser Val Glu Thr Arg Phe Ala Leu Gln Ala Glu
    210                 215                 220

Tyr Arg Ile Lys Met Gly Gly Gln Glu Ile Ser Pro Leu Asn Asp Thr
225                 230                 235                 240

Gly Leu Phe Arg Lys Trp Ala Gly Asp Glu Glu Asp Tyr Leu Ile Lys
                245                 250                 255

Gln Asn Pro Gln Asn Asn Asp Leu Ser Ser Asn Thr Asp Gly Lys Met
                260                 265                 270

Asn Ile Thr Val Asn Pro Asp Tyr Val Ala Pro Lys Glu Leu Tyr Arg
            275                 280                 285

Thr Ala Arg Asn Met Gly Thr Asn Ala Thr Leu Asn Lys Ile Ser Asn
290                 295                 300

Leu Thr Trp Glu Phe Pro Val Asp Ser Gly Phe Thr Tyr Val Leu Arg
305                 310                 315                 320

Leu His Phe Cys Glu Leu Asp Pro Asn Ile Asn Lys Asp Gly Asp Arg
                325                 330                 335

Val Phe Phe Ile Tyr Ile Ala Ser Gln Leu Ala Glu Asn His Ala Asp
                340                 345                 350

Val Met Gln Trp Ser His Asn Gln Lys Gly Leu Ala Val Gln Arg Asn
                355                 360                 365

Tyr Ala Val Leu Ile Pro Lys Asp Asn Thr Gln Lys Lys Val Asn Leu
    370                 375                 380

Ser Leu Arg Met Asp Pro Tyr Ala Thr Asn Asp Lys Thr Thr Tyr Ser
385                 390                 395                 400

Asp Ala Phe Leu Asn Gly Leu Glu Ile Phe Lys Ile Ser Glu Ala Gly
                405                 410                 415

Ser Asn Asn Leu Ala Gly Pro Asn Pro Asp Pro Val Gly Thr Pro His
            420                 425                 430

Asn Asn Ile Pro Ala Pro Lys Gly Asn Arg Ser Ser Lys Ser Gly Thr
            435                 440                 445

Ser Ile Ile Gly Ile Val Ala Gly Val Val Ser Gly Val Val Leu Ile
    450                 455                 460

Ser Leu Ile Ile Leu Phe Leu Ile Val Phe Phe Arg Arg Lys Thr Ile
465                 470                 475                 480

Thr Thr Pro Lys Asp Tyr Asn Lys Ser Lys Ser Ser Ala Thr Ser Lys
                485                 490                 495

Trp Gly Pro Leu Ser Phe Thr Thr Thr Lys Ser Thr Thr Thr Thr Lys
                500                 505                 510

Ser Ser Leu Pro Ser Asp Leu Cys Arg His Phe Ser Leu Pro Glu Ile
            515                 520                 525

Lys Ser Ala Thr Asn Asn Phe Asp Asp Val Phe Ile Val Gly Val Gly
            530                 535                 540

Gly Phe Gly His Val Tyr Lys Gly Tyr Ile Asp Asn Gly Ser Thr Pro
545                 550                 555                 560

Val Ala Ile Lys Arg Leu Lys Pro Gly Ser Gln Gln Gly Ala His Glu
                565                 570                 575
```

```
Phe Met Asn Glu Ile Glu Met Leu Ser Gln Leu Arg His Leu His Leu
            580                 585                 590

Val Ser Leu Ile Gly Tyr Cys Asn Glu Asn Asn Glu Met Ile Leu Val
        595                 600                 605

Tyr Asp Phe Met Ala Arg Gly Thr Leu Arg Asp His Leu Tyr Asn Thr
    610                 615                 620

Asp Asn Pro Pro Leu Thr Trp Lys Gln Arg Leu Gln Ile Cys Ile Gly
625                 630                 635                 640

Ala Ala Arg Gly Leu His Tyr Leu His Thr Gly Ala Lys His Thr Ile
                645                 650                 655

Ile His Arg Asp Val Lys Thr Thr Asn Ile Leu Leu Asp Asp Lys Trp
            660                 665                 670

Val Ala Lys Val Ser Asp Phe Gly Leu Ser Arg Ile Gly Pro Thr Gly
        675                 680                 685

Asn Ala Lys Ala His Val Ser Thr Val Val Lys Gly Ser Ile Gly Tyr
    690                 695                 700

Leu Asp Pro Glu Tyr Tyr Lys Arg Gln Arg Leu Thr Glu Lys Ser Asp
705                 710                 715                 720

Val Tyr Ser Phe Gly Val Val Leu Phe Glu Leu Leu Cys Ala Arg Pro
                725                 730                 735

Pro Leu Ile Arg Thr Ala Glu Lys Lys Gln Val Ser Leu Ala Asp Trp
            740                 745                 750

Ala Arg His Cys Cys Gln Asn Gly Thr Ile Gly Gln Ile Val Asp Pro
        755                 760                 765

Thr Leu Lys Gly Arg Met Ala Pro Glu Cys Leu Arg Lys Phe Cys Glu
    770                 775                 780

Val Ala Val Ser Cys Leu Leu Asp Asp Gly Thr Leu Arg Pro Ser Met
785                 790                 795                 800

Asn Asp Val Val Trp Met Leu Glu Phe Ala Leu Gln Leu Gln Glu Ser
                805                 810                 815

Ala Glu Gln Arg Glu Asn Thr Asn Ile Val Asp Asn Glu Ile Asn Glu
            820                 825                 830

Arg Arg Glu Glu Glu Ala Ser Asp Asp Leu Phe Ser Thr Gly Thr Ser
        835                 840                 845

Val Gly Gln Val Ser Asp Phe Asn Lys Ser Ser Gly Val Val Ser Val
    850                 855                 860

Ser Thr Asp Ser Glu Glu Leu Ser Ser Ser Tyr Lys Glu Ser Asp Lys
865                 870                 875                 880

Leu Met Ser Gly Thr Val Phe Ser Glu Ile Val Asp Pro Lys Pro Arg
                885                 890                 895

<210> SEQ ID NO 2
<211> LENGTH: 2691
<212> TYPE: DNA
<213> ORGANISM: Glycine max

<400> SEQUENCE: 2
atgaggctcc ttagcatcat caccaccctcc ttaacactat tcttccttct tctctttctc      60
tccatagagc tccaagcgta caccccagaa gacaacttca ccatcagttg tggcaccacc     120
gggatagtct tcgacggcca aaggacatgg acggggacg cagacacaaa gtacttatct      180
ggtggtcaag gcagcaccgt tttaacccaa gcagcaacac aagatccttc tgtcaatcaa     240
gttccctaca ccacagcacg ttatcccct tctcagttca attactcctt ccccgttcct     300
gcgggcccca aattcgttcg cctcttcttc tacccggctg attacccttc ctttccccgc     360
```

```
actgatgcct ctttctccgt tcaatctaac ggattcacct tcttaaaagg tttcaacgcc    420
tctctaaacg ctgacgcgga agccaccaaa accatcttca gggaatatgt ggtcaacgtc    480
aacgacggtg agactctcat cctcagcttc actccctcgc aaccaaactc ctacgctttc    540
atcaatggaa tcgaggtgct ttccatgcca agtgatttgt attacacgtc agcaactgac    600
tcaacaggat tcaagttctt gggaagtacc acgctgtaca gcgtagaaac cagatttgcg    660
ctgcaggcgg agtatagaat caaaatggga gggcaagaaa tatcaccact aaacgacacc    720
ggtttgttca ggaaatgggc cggtgacgaa gaagattatt taatcaaaca aaatccacag    780
aataatgatc tttcaagcaa cacgatggt aagatgaaca taaccgtgaa tcctgattac    840
gtggcaccca aggaactcta cagaacagcg cgtaacatgg gcacaaacgc cactctgaac    900
aaaatcagca acctgacttg ggagttcccg gttgattctg gcttcactta cgttctcagg    960
ctccactttt gcgagcttga ccccaatatt aataaagatg gtgacagggt gttcttcatt   1020
tacatagcga gccagttggc tgagaaccac gctgatgtta tgcaatggag ccacaatcag   1080
aaaggtctcg ctgtgcagag aaactatgcc gttttaattc cgaaggacaa tactcagaaa   1140
aaggttaatc tctcgcttcg gatggatcct tatgcaacta atgataaaac gacatacagc   1200
gacgcgttct tgaacggtct cgagatcttc aaaatcagtg aggctgggtc aaacaacctt   1260
gccggaccta acccggaccc ggttcagact ccacacaaca acatacccgc cccaaaggga   1320
aaccgcagca gcaaaagcgg aacgtcgata atcggcatcg tggcaggtgt ggtatccggc   1380
gtcgttttga tctcactcat catccttttc ctcatcgtct tcttccgacg caagacaatc   1440
actacgccca aggactacaa caagtccaag tcctccgcga cctccaagtg gggcccactc   1500
tccttcacaa cgaccaagtc aaccaccacc acgaagtcct ccctccctc cgatctatgc   1560 cgccacttct ccctcccgga gatcaagtcc gccaccaaca acttcgacga cgtcttcatc   1620
gtcggcgtcg gcggattcgg ccacgtgtac aaaggctaca tcgacaacgg ctccaccccc   1680
gtcgccatca agcgcctcaa gccgggttca cagcaaggcg cgcacgagtt catgaacgag   1740
atcgagatgc tatcgcagct ccgccacctc cacctcgtat ctctcatagg ttattgcaac   1800
gagaacaacg agatgatcct cgtctacgac ttcatggcgc gtggaacgct acgcgatcat   1860
ctatacaaca ccgacaaccc cccctttgacg tggaagcagc gcttgcagat ctgcatcggc   1920
gccgcgcgtg gactgcatta cctccacacc ggcgcgaagc acacgatcat ccaccgcgac   1980
gtgaaaacta ccaacatttt gttggatgat aagtgggtgg ccaaggtttc ggacttcggg   2040
ctttcgagaa tcgggcccac gggcaacgcc aaggcccacg tcagcaccgt tgtgaaaggc   2100
agcattgggt atttggaccc ggagtattat aaacgacagc gtttaactga gaaatctgac   2160
gtgtattcct ttgagtggt gctgtttgag ttactctgcg ctcgtccgcc tctgatcaga   2220
actgcggaga agaaacaggt gtcgcttgct gattgggcga ggcactgctg ccaaaatggg   2280
accataggcc agattgtgga ccccactttta aaggggagga tggcgccaga gtgtttgagg   2340
aaattctgcg aggttgcggt gagttgtttg ttggacgacg gaacgctgag gccgtcgatg   2400
aacgacgtcg tttggatgct ggagtttgcg ttgcagttgc aggagagtgc tgagcagcgt   2460
gaaaatacta atattgttga taatgaaatt aatgagagaa gagaggagga ggctagtgat   2520
gatttgttta gtactggaac cagtgtgggc caggtttcgg attttaacaa gagtagcggt   2580
gtggtgagtg tgagtactga tagcgaagag cttagtagta gctacaaaga gagtgataag   2640
ttgatgtctg ggactgtttt ctctgagatt gtggatccaa agccacgttg a            2691
```

<210> SEQ ID NO 3
<211> LENGTH: 635
<212> TYPE: PRT
<213> ORGANISM: Artificial Sequence
<220> FEATURE:
<223> OTHER INFORMATION: Artificial Protein Corresponding to Mutant GmLMM1

<400> SEQUENCE: 3

```
Met Arg Leu Leu Ser Ile Ile Thr Thr Ser Leu Thr Leu Phe Phe Leu
1               5                   10                  15

Leu Leu Phe Leu Ser Ile Glu Leu Gln Ala Tyr Thr Pro Glu Asp Asn
            20                  25                  30

Phe Thr Ile Ser Cys Gly Thr Thr Gly Ile Val Phe Asp Gly Gln Arg
        35                  40                  45

Thr Trp Thr Gly Asp Ala Asp Thr Lys Tyr Leu Ser Gly Gly Gln Gly
    50                  55                  60

Ser Thr Val Leu Thr Gln Ala Ala Thr Gln Asp Pro Ser Val Asn Gln
65                  70                  75                  80

Val Pro Tyr Thr Thr Ala Arg Leu Ser Pro Ser Gln Phe Asn Tyr Ser
                85                  90                  95

Phe Pro Val Ser Ala Gly Pro Lys Phe Val Arg Leu Phe Phe Tyr Pro
            100                 105                 110

Ala Asp Tyr Pro Ser Phe Pro Arg Thr Asp Ala Ser Phe Ser Val Gln
        115                 120                 125

Ser Asn Gly Phe Thr Phe Leu Lys Gly Phe Asn Ala Ser Leu Asn Ala
    130                 135                 140

Asp Ala Glu Ala Thr Lys Thr Ile Phe Arg Glu Tyr Val Val Asn Val
145                 150                 155                 160

Asn Asp Gly Glu Thr Leu Ile Leu Ser Phe Thr Pro Ser Gln Pro Asn
                165                 170                 175

Ser Tyr Ala Phe Ile Asn Gly Ile Glu Val Leu Ser Met Pro Ser Asp
            180                 185                 190

Leu Tyr Tyr Thr Ser Ala Thr Asp Ser Thr Gly Phe Lys Phe Leu Gly
        195                 200                 205

Ser Thr Thr Leu Tyr Ser Val Glu Thr Arg Phe Ala Leu Gln Ala Glu
    210                 215                 220

Tyr Arg Ile Lys Met Gly Gly Gln Glu Ile Ser Pro Leu Asn Asp Thr
225                 230                 235                 240

Gly Leu Phe Arg Lys Trp Ala Gly Asp Glu Glu Asp Tyr Leu Ile Lys
                245                 250                 255

Gln Asn Pro Gln Asn Asn Asp Leu Ser Ser Asn Thr Asp Gly Lys Met
            260                 265                 270

Asn Ile Thr Val Asn Pro Asp Tyr Val Ala Pro Lys Glu Leu Tyr Arg
        275                 280                 285

Thr Ala Arg Asn Met Gly Thr Asn Ala Thr Leu Asn Lys Ile Ser Asn
    290                 295                 300

Leu Thr Trp Glu Phe Pro Val Asp Ser Gly Phe Thr Tyr Val Leu Arg
305                 310                 315                 320

Leu His Phe Cys Glu Leu Asp Pro Asn Ile Asn Lys Asp Gly Asp Arg
                325                 330                 335

Val Phe Phe Ile Tyr Ile Ala Ser Gln Leu Ala Glu Asn His Ala Asp
            340                 345                 350

Val Met Gln Trp Ser His Asn Gln Lys Gly Leu Ala Val Gln Arg Asn
        355                 360                 365
```

Tyr Ala Val Leu Ile Pro Lys Asp Asn Thr Gln Lys Val Asn Leu
370             375                 380

Ser Leu Arg Met Asp Pro Tyr Ala Thr Asn Asp Lys Thr Thr Tyr Ser
385                 390                 395                 400

Asp Ala Phe Leu Asn Gly Leu Glu Ile Phe Lys Ile Ser Glu Ala Gly
            405                 410                 415

Ser Asn Asn Leu Ala Gly Pro Asn Pro Asp Pro Val Gln Thr Pro His
            420                 425                 430

Asn Asn Ile Pro Ala Pro Lys Gly Asn Arg Ser Ser Lys Ser Gly Thr
            435                 440                 445

Ser Ile Ile Gly Ile Val Ala Gly Val Val Ser Gly Val Val Leu Ile
450                 455                 460

Ser Leu Ile Ile Leu Phe Leu Ile Val Phe Phe Arg Arg Lys Thr Ile
465                 470                 475                 480

Thr Thr Pro Lys Asp Tyr Asn Lys Ser Lys Ser Ser Ala Thr Ser Lys
            485                 490                 495

Trp Gly Pro Leu Ser Phe Thr Thr Thr Lys Ser Thr Thr Thr Thr Lys
            500                 505                 510

Ser Ser Leu Pro Ser Asp Leu Cys Arg His Phe Ser Leu Pro Glu Ile
515                 520                 525

Lys Ser Ala Thr Asn Asn Phe Asp Asp Val Phe Ile Val Gly Val Gly
530                 535                 540

Gly Phe Gly His Val Tyr Lys Gly Tyr Ile Asp Asn Gly Ser Thr Pro
545                 550                 555                 560

Val Ala Ile Lys Arg Leu Lys Pro Gly Ser Gln Gln Gly Ala His Glu
            565                 570                 575

Phe Met Asn Glu Ile Glu Met Leu Ser Gln Leu Arg His Leu His Leu
            580                 585                 590

Val Ser Leu Ile Gly Tyr Cys Asn Glu Asn Asn Glu Met Ile Leu Val
            595                 600                 605

Tyr Asp Phe Met Ala Arg Gly Thr Leu Arg Asp His Leu Tyr Asn Thr
610                 615                 620

Asp Asn Pro Pro Leu Thr Trp Lys Gln Arg Leu
625                 630                 635

```
<210> SEQ ID NO 4
<211> LENGTH: 2691
<212> TYPE: DNA
<213> ORGANISM: Artificial Sequence
<220> FEATURE:
<223> OTHER INFORMATION: DNA Sequence for Mutant GmLMM1

<400> SEQUENCE: 4
atgaggctcc ttagcatcat caccaccctcc ttaacactat tcttccttct tctctttctc     60
tccatagagc tccaagcgta caccccagaa gacaacttca ccatcagttg tggcaccacc    120
gggatagtct tcgacggcca aaggacatgg acggggacg cagacacaaa gtacttatct    180
ggtggtcaag gcagcaccgt tttaacccaa gcagcaacac aagatccttc tgtcaatcaa    240
gttccctaca ccacagcacg gttatcccct tctcagttca attactcctt ccccgttttct   300 gcgggcccca aattcgttcg cctcttcttc tacccggctg attacccttc ctttccccgc    360
actgatgcct ctttctccgt tcaatctaac ggattcacct tcttaaaagg tttcaacgcc    420
tctctaaacg ctgacgcgga agccaccaaa accatcttca gggaatatgt ggtcaacgtc    480
aacgacggtg agactctcat cctcagcttc actccctcgc aaccaaactc ctacgctttc    540
```

```
atcaatggaa tcgaggtgct ttccatgcca agtgatttgt attacacgtc agcaactgac    600
tcaacaggat tcaagttctt gggaagtacc acgctgtaca gcgtagaaac cagatttgcg    660
ctgcaggcgg agtatagaat caaaatggga gggcaagaaa tatcaccact aaacgacacc    720
ggtttgttca ggaaatgggc cggtgacgaa gaagattatt taatcaaaca aaatccacag    780
aataatgatc tttcaagcaa cacggatggt aagatgaaca taaccgtgaa tcctgattac    840
gtggcaccca aggaactcta cagaacagcg cgtaacatgg cacaaacgc cactctgaac     900 aaaatcagca acctgacttg ggagttcccg gttgattctg cttcactta cgttctcagg     960 ctccactttt gcgagcttga ccccaatatt aataaagatg gtgacagggt gttcttcatt   1020
tacatagcga gccagttggc tgagaaccac gctgatgtta tgcaatggag ccacaatcag   1080
aaaggtctcg ctgtgcagag aaactatgcc gttttaattc cgaaggacaa tactcagaaa   1140
aaggttaatc tctcgcttcg gatggatcct tatgcaacta atgataaaac gacatacagc   1200
gacgcgttct tgaacggtct cgagatcttc aaaatcagtg aggctgggtc aaacaacctt   1260
gccggaccta acccggaccc ggttcagact ccacacaaca acataccgc cccaaaggga    1320 aaccgcagca gcaaaagcgg aacgtcgata atcggcatcg tggcaggtgt ggtatccggc   1380
gtcgttttga tctcactcat catccttttc ctcatcgtct tcttccgacg caagacaatc   1440
actacgccca aggactacaa caagtccaag tcctccgcga cctccaagtg gggcccactc   1500
tccttcacaa cgaccaagtc aaccaccacc acgaagtcct ccctcccctc cgatctatgc   1560
cgccacttct ccctcccgga gatcaagtcc gccaccaaca acttcgacga cgtcttcatc   1620
gtcggcgtcg gcggattcgg ccacgtgtac aaaggctaca tcgacaacgg ctccacccc    1680 gtcgccatca gcgcctcaa gccgggttca gcaacaaggcg cgcacgagtt catgaacgag   1740
atcgagatgc tatcgcagct ccgccacctc cacctcgtat ctctcatagg ttattgcaac   1800
gagaacaacg agatgatcct cgtctacgac ttcatggcgc gtggaacgct acgcgatcat   1860
ctatacaaca ccgacaaccc cccttttgacg tggaagcagc gcttgtagat ctgcatcggc   1920
gccgcgcgtg gactgcatta cctccacacc ggcgcgaagc acacgatcat ccaccgcgac   1980
gtgaaaacta ccaacatttt gttggatgat aagtgggtgg ccaaggtttc ggacttcggg   2040
ctttcgagaa tcgggcccac gggcaacgcc aaggcccacg tcagcaccgt tgtgaaaggc   2100
agcattgggt atttggaccc ggagtattat aaacgacagc gtttaactga aaatctgac    2160 gtgtattcct ttggagtggt gctgtttgag ttactctgcg ctcgtccgcc tctgatcaga   2220
actgcggaga agaaacaggt gtcgcttgct gattgggcga ggcactgctg ccaaaatggg   2280
accataggcc agattgtgga ccccactta aaggggagga tggcgccaga gtgtttgagg    2340
aaattctgcg aggttgcgt gagttgtttg ttggacgacg gaacgctgag gccgtcgatg    2400
aacgacgtcg tttggatgct ggagtttgcg ttgcagttgc aggagagtgc tgagcagcgt   2460
gaaaatacta atattgttga taatgaaatt aatgagagaa gagaggagga ggctagtgat   2520
gatttgttta gtactggaac cagtgtgggc caggtttcgg attttaacaa gagtagcggt   2580
gtggtgagtg tgagtactga tagcgaagag cttagtagta gctacaaaga gagtgataag   2640
ttgatgtctg ggactgtttt ctctgagatt gtggatccaa agccacgttg a             2691
```

<210> SEQ ID NO 5
<211> LENGTH: 20
<212> TYPE: RNA
<213> ORGANISM: Artificial Sequence
<220> FEATURE:

```
<223> OTHER INFORMATION: gRNA sequence for CRISPR/Cas9

<400> SEQUENCE: 5
gcgaggcacu gcugccaaaa                                                20
```

USE OF SOYBEAN BROAD-SPECTRUM DISEASE RESISTANCE RELATED GENE

CROSS-REFERENCE TO RELATED APPLICATIONS

This application is a national phase entry under 35 U.S.C. § 371 of International Patent Application PCT/CN2020/105801, filed Jul. 30, 2020, designating the United States of America and published as International Patent Publication WO 2021/082567 A1 on May 6, 2021, which claims the benefit under Article 8 of the Patent Cooperation Treaty to Chinese Patent Application Serial No. 201911044883.5, filed Oct. 30, 2019.

TECHNICAL FIELD

The present disclosure relates to the technical field of plant genetic engineering, and specifically relates to the use of a soybean disease resistance related gene GmLMM1 in regulating the PTI immune response of plants and increasing the pathogen resistance of plants.

STATEMENT ACCORDING TO 37 C.F.R. § 1.821(c) or (e)—SEQUENCE LISTING SUBMITTED AS A TXT AND PDF FILES

Pursuant to 37 C.F.R. § 1.821(c) or (e), files containing a TXT version and a PDF version of the Sequence Listing have been submitted concomitant with this application, the contents of which are hereby incorporated by reference.

BACKGROUND

Soybean is one of the main sources of oils and vegetable proteins worldwide. With the rapid growth of the world's population, the demand for soybeans in food, feed and industrial production has also steadily increased. However, on a global scale, the occurrence of persistent diseases has severely affected the yield and quality of soybean. Soybean diseases such as bacterial blight of soybeans disease and *Phytophthora* root rot have caused great losses to the global soybean yield and quality, wherein, *Phytophthora sojae* (*P. sojae*) disease is one of the most harmful diseases in soybean production, which seriously harms soybean production, and the diseases caused by it are widespread in all major soybean planting areas. *Phytophthora sojae* can infect seeds, roots, stems and leaves, and for varieties that are highly sensitive to *Phytophthora sojae*, this disease can result in no soybean at all. Traditional disease control mainly relies on chemical methods and breeding methods. However, the evolution speed of pathogens has surpassed the speed of improvement and optimization of these control methods, and thus these traditional control methods cannot play an effective role in disease control. Therefore, the use of disease-resistant genetic engineering breeding is the most effective way to solve this problem.

The ability of plants to resist diseases and insect pests is closely related to their own immune system. Therefore, it is very important to study the immune system of soybean and explore how the soybean can protect themselves against microbial pathogens. Meanwhile, it is significant to study the disease resistance mechanism of soybean for breeding new varieties of disease-resistant soybean.

BRIEF SUMMARY

In order to solve the technical problems existing in the prior art, the purpose of the present disclosure is to provide the use of a soybean GmLMM1 gene in regulating the PTI immune response and the pathogen resistance of plants.

In order to achieve the above purposes, the technical solution of the present disclosure is as follows:

In the present disclosure, a soybean plant related to broad-spectrum disease resistance is obtained by screening an artificial chemical mutagenesis soybean mutant library, and named as GmLMM1(*Glycine max* lesion mimic mutant 1). Through map-based cloning and sequencing analysis, it was confirmed that the enhancement of broad-spectrum disease resistance of soybean was caused by the artificial mutagenic changes of Glyma.13G054400 gene sequence (the amino acid sequence of the protein encoded thereby is represented by SEQ ID NO. 1, and the CDS sequence is represented by SEQ ID NO. 2). The amino acid sequence of the protein encoded by the gene after artificial mutagenesis is represented by SEQ ID NO. 3, and the CDS sequence is represented by SEQ ID NO. 4. It is found in the present disclosure that GmLMM1 gene negatively regulates the PTI immune response and the pathogen resistance of plants.

In the first aspect, the present disclosure provides the use of a soybean GmLMM1 gene or its mutant gene or protein encoded by the soybean GmLMM1 gene or its mutant gene in the regulation of the pathogen resistance of plants.

In the second aspect, the present disclosure provides the use of a soybean GmLMM1 gene or its mutant gene or protein encoded by the soybean GmLMM1 gene or its mutant gene in the regulation of the PTI immune response of plants.

In the above uses, by reducing the expression of the GmLMM1 gene in plants, the pathogen resistance of plants can be increased and the PTI immune response of plants can be enhanced.

In the third aspect, the present disclosure provides the use of a soybean GmLMM1 gene or its mutant gene or protein encoded by the soybean GmLMM1 gene or its mutant gene in plant genetic breeding or transgenic plant preparation.

Preferably, the transgenic plant is a disease-resistant transgenic plant, and more preferably, a transgenic plant is resistant to *Phytophthora* and bacterial blight disease.

In the present disclosure, the protein encoded by the soybean GmLMM1 gene has any one of the following amino acid sequences:

(1) an amino acid sequence represented by SEQ ID NO. 1;

(2) an amino acid sequence obtained by substitution, insertion or deletion of one or more amino acids in the amino acid sequence represented by SEQ ID NO. 1, and having the same function as the amino acid sequence represented by SEQ ID NO. 1; and (3) an amino acid sequence having at least 80% homology to the amino acid sequence represented by SEQ ID NO. 1; preferably, the homology is at least 90%, more preferably 95%.

In the present disclosure, the protein encoded by the mutant gene of the soybean GmLMM1 gene has any one of the following amino acid sequences:

(1) an amino acid sequence represented by SEQ ID NO. 3;

(2) an amino acid sequence obtained by substitution, insertion or deletion of one or more amino acids in the amino acid sequence represented by SEQ ID NO. 3, and having the same function as the amino acid sequence represented by SEQ ID NO. 3; and (3) an amino acid sequence having at least 80% homology to the amino acid sequence represented by SEQ ID NO. 3; preferably, the homology is at least 90%, more preferably 95%.

In the present disclosure, the CDS of the soybean GmLMM1 gene has any one of the following nucleotide sequences:
(1) a nucleotide sequence represented by SEQ ID NO. 2; and
(2) a nucleotide sequence obtained by substitution, insertion or deletion of one or more nucleotides in the nucleotide sequence represented by SEQ ID NO. 2, and encoding the same functional protein as SEQ ID NO. 2.

In the present disclosure, the CDS of the mutant gene of the soybean GmLMM1 gene has any one of the following nucleotide sequences:
(1) a nucleotide sequence represented by SEQ ID NO. 4; and
(2) a nucleotide sequence obtained by substitution, insertion or deletion of one or more nucleotides in the nucleotide sequence represented by SEQ ID NO. 4, and encoding the same functional protein as SEQ ID NO. 4.

The above amino acid sequence represented by SEQ ID NO. 1 is the amino acid sequence of the protein encoded by the soybean GmLMM1 gene. A person skilled in the art may obtain a mutant of the protein encoded by GmLMM1 gene with the same activity as the protein encoded by the GmLMM1 gene disclosed in the present disclosure by substitution, deletion and/or addition of one or more amino acids without affecting the activity, according to the amino acid sequence disclosed in the present disclosure as well as conventional technical means in the art such as conservative substitutions of amino acids.

The above nucleotide sequence represented by SEQ ID NO. 2 is the CDS sequence of GmLMM1 gene in soybean. Taking into account the degeneracy of codons and the preference of codons in different species, a person skilled in the art can use codons suitable for expression in specific species as needed.

The above amino acid sequence represented by SEQ ID NO. 3 is the amino acid sequence of the protein encoded by the mutant gene of soybean GmLMM1 gene. A person skilled in the art may obtain a mutant of the protein encoded by the mutant gene of the GmLMM1 gene with the same activity as the protein encoded by the mutant gene of the GmLMM1 gene disclosed in the present disclosure by substitution, deletion and/or addition of one or more amino acids without affecting the activity, according to the amino acid sequence disclosed in the present disclosure as well as conventional technical means in the art such as conservative substitution of amino acids.

The above nucleotide sequence represented by SEQ ID NO. 4 is the CDS sequence of the mutant gene of the GmLMM1 gene in soybean. Taking into account the degeneracy of codons and the preference of codons in different species, a person skilled in the art can use codons suitable for expression in specific species as needed.

Preferably, a transgenic plant with the GmLMM1 gene knocked out is obtained by CRISPR/Cas9 technology, and the obtained transgenic plant is a disease-resistant transgenic plant.

As an example, the present disclosure provides a gRNA for targeting a specific position of the GmLMM1 gene, and the gRNA comprises the nucleotide sequence represented by SEQ ID NO. 5. The gRNA can cooperate with gene editing tools such as Cas9 to realize the knockout of soybean GmLMM1 gene.

The use of the above-mentioned GmLMM1 gene or its mutant gene or protein encoded by the GmLMM1 gene or its mutant gene can be applied in the form of GmLMM1 gene or its mutant gene or protein itself encoded by the soybean GmLMM1 gene or its mutant gene, or in the form of an expression cassette and a vector containing the protein encoded by the GmLMM1 gene or the protein encoded by the mutant gene of the GmLMM1 gene, and a host cell containing the expression cassette or the vector.

In the fourth aspect, the present disclosure provides a method for regulating the pathogen resistance of plants, comprising: regulating the expression of GmLMM1 gene in soybean to obtain a mutant with increased pathogen resistance.

The protein encoded by the soybean GmLMM1 gene has any one of the following amino acid sequences:
(1) an amino acid sequence represented by SEQ ID NO. 1;
(2) an amino acid sequence obtained by substitution, insertion or deletion of one or more amino acids in the amino acid sequence represented by SEQ ID NO. 1, and having the same function as the amino acid sequence represented by SEQ ID NO. 1; and
(3) an amino acid sequence having at least 80% homology to the amino acid sequence represented by SEQ ID NO. 1; preferably, the homology is at least 90%; more preferably 95%.

The protein encoded by the mutant gene of the soybean GmLMM1 gene has any one of the following amino acid sequences:
(1) an amino acid sequence represented by SEQ ID NO. 3;
(2) an amino acid sequence obtained by substitution, insertion or deletion of one or more amino acids in the amino acid sequence represented by SEQ ID NO. 3, and having the same function as the amino acid sequence represented by SEQ ID NO. 3; and
(3) an amino acid sequence having at least 80% homology to the amino acid sequence represented by SEQ ID NO. 3; preferably, the homology is at least 90%; more preferably 95%.

Preferably, the above method comprises: reducing the expression of the GmLMM1 gene in the plant to increase the pathogen resistance of the plant.

The aforementioned reduction in the expression of the GmLMM1 gene in plants can be achieved by conventional technical means in the art, such as: CRISPR/Cas9 technology, which can be used to knock out the GmLMM1 gene in plants.

Preferably, the present disclosure utilizes the CRISPR/Cas9 technology to knock out the GmLMM1 gene in the plant with a nucleotide sequence represented by SEQ ID NO. 5 as the gRNA, which can efficiently knock out the GmLMM1 gene in the plant.

In the present disclosure, the plant is a monocotyledonous plant or a dicotyledonous plant. The plants include but are not limited to soybean, wheat, rice, corn, cotton, rape, peanut, legume crops, vegetable crops and the like.

The beneficial effects of the present disclosure lie in that:
In the present disclosure, the GmLMM1 gene involved in plant immune response and pathogen resistance regulation is cloned in soybean for the first time. GmLMM1 gene can negatively regulate plant PTI immune response and pathogen resistance: by reducing the expression of the GmLMM1 gene, the PTI immune response of plants can be effectively enhanced and the pathogen resistance of plants can be increased, which reduces pathogen susceptibility and incidence of disease. The cloning and functional analysis of the GmLMM1 gene is a breakthrough in the exploration for soybean disease resistance mechanism, providing important gene foundations and theoretical support for research on the related mechanisms of plant disease resistance, and providing valuable gene resources for advancing the research and application of plant defense systems and for breeding new soybean varieties with high disease resistance. The GmLMM1 gene and protein encoded thereby have an important application value in the genetic engineering breeding of soybean disease resistance.

DETAILED DESCRIPTION

The preferred embodiments of the present disclosure will be described in detail below in conjunction with Examples. It should be understood that the following Examples are given for illustrative purposes only, and are not intended to limit the scope of the present disclosure. A person skilled in the art can make various modifications and substitutions to the present disclosure without departing from the purpose and spirit of the present disclosure.

The experimental methods used in the following Examples are conventional methods unless otherwise specified.

The materials and reagents used in the following Examples can be obtained from commercial sources unless otherwise specified.

Example 1: Identification of *Phytophthora* Resistance Phenotype of GmLMM1 Mutant to *Phytophthora*

Figure 1:
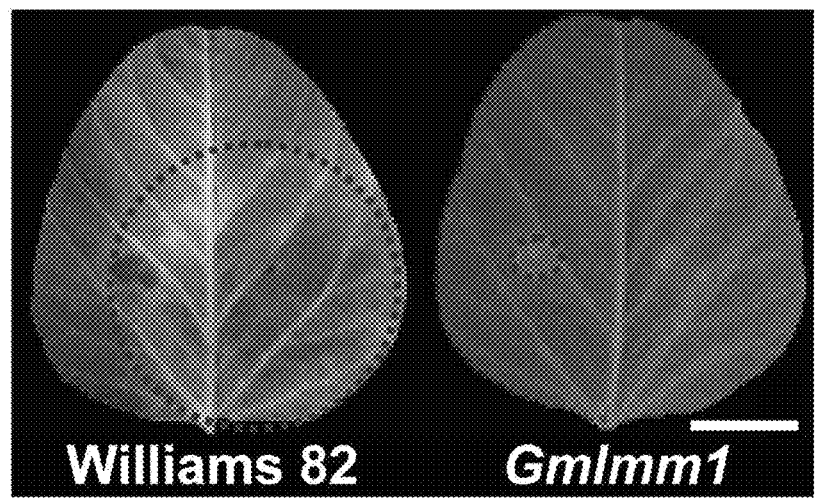
FIG. 1 shows the observation of pathogen infection under ultraviolet light 48 hours after wild-type Williams 82 leaves and GmLMM1 mutant leaves were inoculated with *Phytophthora sojae* (*P. sojae*) P7076 hyphae blocks in Example 1 of the present disclosure. Scale, 1 cm. Inside the dashed circle are the lesions infected by pathogen.
Figure 2:
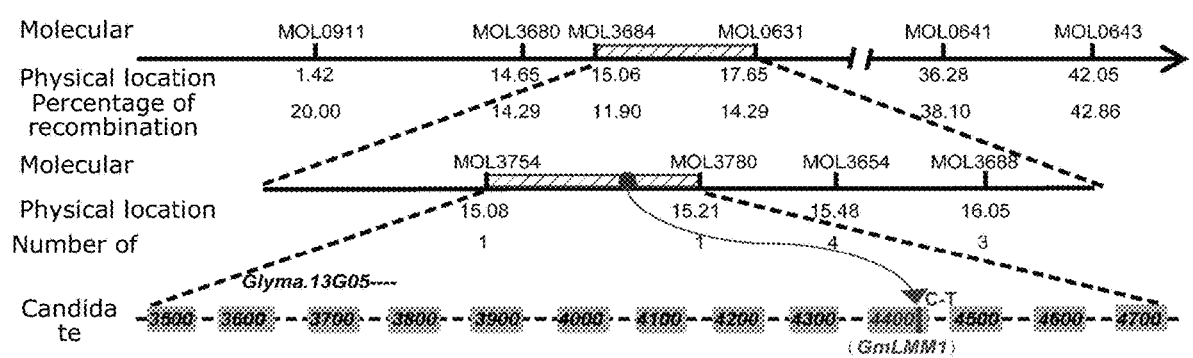
FIG. 2 shows the location of GmLMM1 gene on soybean chromosome 13 in Example 1 of the present disclosure.

The mutant GmLMM1 was obtained by screening the mutant library obtained by performing EMS mutagenesis on Williams 82. *Phytophthora sojae* (*P. sojae*) P7076 hyphae blocks were used to inoculate leaves of wild-type "Williams 82" and leaves of GmLMM1 mutant. After 48 hours of infection, pathogen infected leaves were observed under ultraviolet light (FIG. 1). The results show that the pathogen infected area of the mutant GmLMM1 is significantly smaller than that of the wild-type Williams 82, indicating that the mutant GmLMM1 significantly improves resistance to soybean *Phytophthora* compared with the wild-type Williams 82. The above experimental results indicate that the GmLMM1 mutant has the characteristics of being resistant to soybean *Phytophthora*. Therefore, it is speculated that the GmLMM1 gene may be involved in the regulation of plant immune response. By using the F2 segregated population obtained by the hybridization of GmLMM1 and "Hedou 12" for gene mapping, it was found that the GmLMM1 gene was located in the 131 kb interval between 15.08 Mb and 15.21 Mb on chromosome 13 (FIG. 2), and in combination with the whole genome resequencing result of GmLMM1, it is finally determined that the GmLMM1 gene is Glyma.13G054400 (the amino acid sequence of the protein encoded thereby is represented by SEQ ID NO. 1, and the CDS sequence is represented by SEQ ID NO. 2), and there is a single-base mutation (C to T) in the second exon region of Glyma.13G054400 (GmLMM1) gene in GmLMM1 (the amino acid sequence of the protein encoded by the mutant gene is represented by SEQ ID NO. 3, and the CDS sequence of the mutant gene is represented by SEQ ID NO. 4) (FIG. 2).

Figure 3:
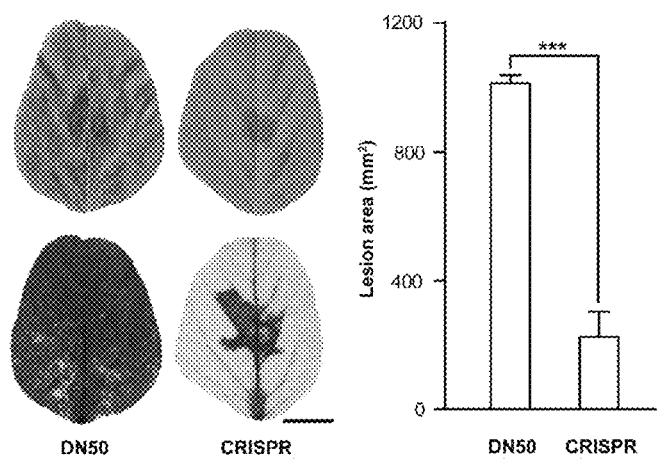
FIG. 3 shows the observation of infection and the statistics of the lesion area 60 hours after of the leaves of the transgenic plant with GmLMM1 gene knocked out were inoculated with *Phytophthora sojae* (*P. sojae*) P7076 hyphae blocks in Example 2 of the present disclosure. Scale, 1 cm. *** represents significant difference at a level of $p<0.001$.
Figure 4:
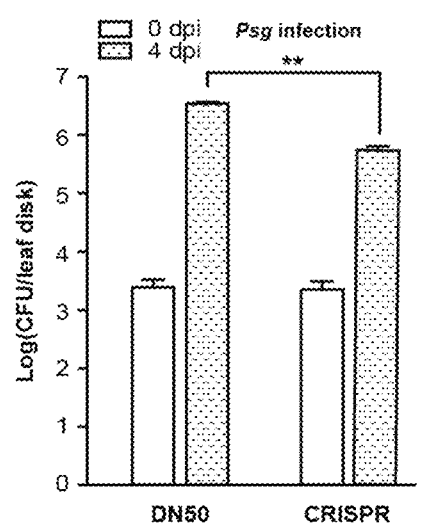
FIG. 4 shows the statistics of the bacterial colony number 4 days after the leaves of the transgenic plant with GmLMM1 gene knocked out were inoculated with pathogen *Pseudomonas syringae* pv. glycinea (Psg) of bacterial blight of soybeans in Example 2 of the present disclosure. ** represents significant difference at a level of $p<0.01$.
Figure 5:
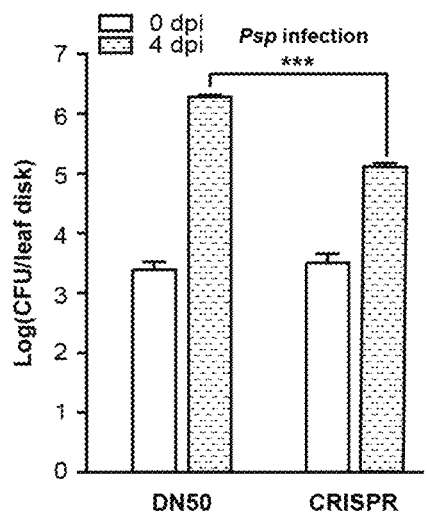
FIG. 5 shows the statistics of the bacterial colony number 4 days after the leaves of transgenic plant with GmLMM1 gene knocked out were inoculated with pathogen *Pseudomonas syringae* pv. phaseolicola (Psp) of halo blight of the common bean, *Phaseolus vulgaris* in Example 2 of the present disclosure. *** represents significant difference at a level of $p<0.001$.

Example 2: Significantly Enhanced Pathogen Resistance in the Transgenic Plants with GmLMM1 Gene Knocked Out A CRISPR/Cas9 recombinant plasmid with gRNA (sequence as represented by SEQ ID NO. 5) driven by GmU6 promoter and Cas9 protein driven by GmUbi3 promoter was constructed, and the recombinant plasmid was introduced into the wild-type soybean variety Dongnong 50 (DN50) with an *Agrobacterium*-mediated genetic transformation system. After genetic transformation, T1 generation transgenic plants were finally obtained. *Phytophthora sojae* (*P. sojae*) P7076 hyphae blocks were used to inoculate leaves of wild-type DN50 and leaves of transgenic plant CRISPR with GmLMM1 gene knocked out. After 60 hours of infection, trypan blue staining was used to observe the difference in infection, and the statistics of the area of lesion formation was performed (FIG. 3). The results show that the lesion area of the leaves of the transgenic plant CRISPR is significantly smaller than the lesion area of the wild-type DN50, indicating that the resistance to soybean *Phytophthora* is significantly improved after the GmLMM1 gene is knocked out. The leaves of wild-type DN50 and the leaves of the transgenic plant CRISPR with GmLMM1 gene knocked out were inoculated with the pathogen *Pseudomonas syringae* pv. glycinea (Psg) of bacterial blight of soybeans (FIG. 4) and the pathogen *Pseudomonas syringae* pv.

phaseolicola (Psp) of halo blight of the common bean, *Phaseolus vulgaris* (FIG. 5) by injection, and after 4 days, statistical analysis of the number of pathogen colonies formed was performed. Statistical analysis results show that the number of pathogen colonies in the leaves of the transgenic plant CRISPR is significantly less than the number of colonies in the leaves of the wild-type DN50, indicating that the resistance to bacterial blight of soybeans and halo blight of the common bean, *Phaseolus vulgaris* is significantly improved after the GmLMM1 gene is knocked out. The results of genetic transformation experiment further illustrate the important role of GmLMM1 gene in immune response. The discovery of new functions of GmLMM1 gene provides valuable genetic resources for plant genetic breeding.

Example 3: Inhibition of PTI Immune Response of Plants by GmLMM1 Gene

Figure 6:
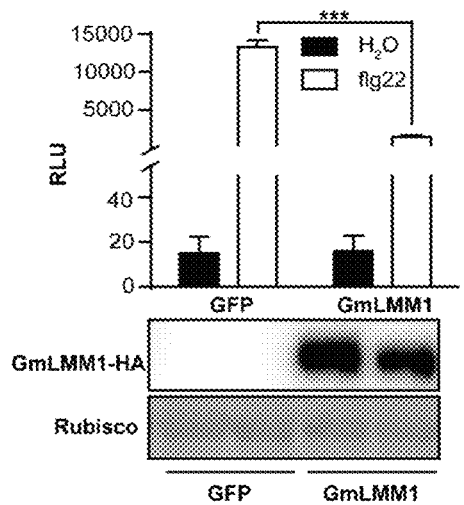
FIG. 6 shows that GmLMM1 inhibits the active oxygen burst in the PTI immune response induced by flg22 in Example 3 of the present disclosure. The active oxygen burst of tobacco leaves treated with 1 μM flg22 or water-treated and transiently expressing GFP or GmLMM1 gene was shown, wherein GFP represents the control group, GmLMM1-HA represents the experimental group, $H_2O$ represents the blank control group treated with $H_2O$, flg22 represents treatment with flg22 small peptide, and the expression of GmLMM1 was detected by Western blot with Rubisco as the internal reference.

*Agrobacterium* was injected into tobaccos to transiently express GFP (control group) and GmLMM1 (experimental group), and after 24 hours, water and flg22 (a small peptide containing 22 amino acids from conserved N-terminus of flagellin and commonly used in plant immunity research) were used for treatment, respectively. The active oxygen burst was detected after treatment, and it was found that transient overexpression of GmLMM1 can inhibit the active oxygen burst induced by flg22 (FIG. 6). The above experiments show that the GmLMM1 gene can inhibit the active oxygen burst in the PTI immune response, and negatively regulate the PTI immune response of plants.

Although the present disclosure has been described in detail with general descriptions, specific embodiments and tests above, it is obvious to a person skilled in the art that some modifications or improvements can be made on the basis of the present disclosure. Therefore, all these modifications or improvements made without departing from the spirit of the present disclosure belong to the scope of the present disclosure.

INDUSTRIAL APPLICABILITY

The present disclosure provides the use of a soybean broad-spectrum disease resistance related gene GmLMM1. In the present disclosure, the GmLMM1 gene, which is involved in the regulation of PTI immune response, *Phytophthora* resistance, bacterial blight of soybeans disease, halo blight of the common bean, *Phaseolus vulgaris*, etc., is cloned in soybeans. The PTI immune response and pathogen resistance of plants can be negatively regulated by the GmLMM1 gene; and by reducing the expression of the GmLMM1 gene, the PTI immune response of plants can be effectively enhanced, and the pathogen resistance of plants can be increased. The cloning and functional discovery of the GmLMM1 gene provide important gene foundations and theoretical support for research on the related mechanisms of soybean disease resistance, and provide valuable gene resources for advancing the research and application of plant defense systems and for breeding new soybean varieties with high disease resistance, and thus have an important application value and prospects in the genetic engineering-based breeding of soybean disease resistance.

What is claimed is:

1. A method for enhancing the pattern-triggered immunity (PTI) immune response of a soybean plant, the method comprising:
   reducing the expression of a GmLMM1 gene or a mutant GmLMM1 gene or a protein encoded by the GmLMM1 gene or the mutant GmLMM1 gene in the plant by knocking out the GmLMM1 gene or the mutant GmLMM1 gene using CRISPR/Cas9 technology, wherein
   the protein encoded by the GmLMM1 gene has the amino acid sequence of SEQ ID NO:1, and
   the protein encoded by the mutant GmLMM1 gene has the amino acid sequence of SEQ ID NO: 3,
   so as to enhance the PTI immune response of the plant.

2. A method for plant genetic breeding or transgenic plant preparation, the method comprising:
   regulating the expression of a soybean GmLMM1 gene or a mutant soybean GmLMM1 gene or a protein encoded by the soybean GmLMM1 gene or the mutant soybean GmLMM1 gene in a soybean plant, wherein
   the protein encoded by the soybean GmLMM1 gene has the amino acid sequence of SEQ ID NO: 1, and
   the protein encoded by the mutant soybean GmLMM1 gene has the amino acid sequence of SEQ ID NO: 3.

3. The method according to claim 1, wherein the CRISPR/Cas9 technology comprises the gRNA comprising the nucleotide sequence represented by SEQ ID NO: 5.

* * * * *